United States Patent
Chornet et al.

(10) Patent No.: US 8,080,693 B2
(45) Date of Patent: Dec. 20, 2011

(54) PRODUCTION OF ETHANOL FROM METHANOL

(75) Inventors: Esteban Chornet, Sherbrooke (CA); Boris Valsecchi, Sherbrooke (CA); Yasmin Avila, Montréal (CA); Betty Nguyen, Montréal (CA); Jean-Michel Lavoie, Canton de Hatley (CA)

(73) Assignee: Enerkem, Inc., Montreal (Quebec) (CA)

( * ) Notice: Subject to any disclaimer, the term of this patent is extended or adjusted under 35 U.S.C. 154(b) by 152 days.

(21) Appl. No.: 12/378,903

(22) Filed: Feb. 20, 2009

(65) Prior Publication Data
US 2009/0326080 A1 Dec. 31, 2009

Related U.S. Application Data

(63) Continuation-in-part of application No. 12/228,572, filed on Aug. 14, 2008, now abandoned.

(60) Provisional application No. 61/067,403, filed on Feb. 28, 2008.

(51) Int. Cl.
*C07C 27/06* (2006.01)

(52) U.S. Cl. ..................... 568/885; 568/902.2

(58) Field of Classification Search .................. 568/885, 568/902.2
See application file for complete search history.

(56) References Cited

U.S. PATENT DOCUMENTS

| | | | | |
|---|---|---|---|---|
| 4,424,384 A | * | 1/1984 | Lin et al. | 568/902.2 |
| 4,454,358 A | * | 6/1984 | Kummer et al. | 568/885 |
| 4,727,200 A | * | 2/1988 | Wegman et al. | 568/902 |
| 5,414,161 A | * | 5/1995 | Uhm et al. | 568/885 |

FOREIGN PATENT DOCUMENTS

| | | |
|---|---|---|
| GB | 2162172 | 1/1986 |
| WO | WO83/03409 | 10/1983 |

* cited by examiner

*Primary Examiner* — Sikarl Witherspoon
(74) *Attorney, Agent, or Firm* — Elliot M. Olstein; Raymond J. Lillie

(57) ABSTRACT

A process for converting methanol to ethanol which comprises reacting methanol and carbon monoxide in the presence of a catalyst to produce a product comprising at least 25 mole % methyl acetate and, in some instances, acetic acid. The acetic acid then is reacted with at least one alcohol to produce at least one acetate selected from methyl acetate, ethyl acetate, and butyl acetate. The at least one acetate (if produced) and the methyl acetate produced as a result of reacting methanol and carbon monoxide then are hydrogenated to produce ethanol. Syngas may be produced from biomass to produce all or a portion of the methanol, hydrogen, and carbon monoxide requirements for the process.

68 Claims, No Drawings

PRODUCTION OF ETHANOL FROM METHANOL

This application is a continuation-in-part of application Ser. No. 12/228,572, filed Aug. 14, 2008 now abandoned, which is a continuation-in-part of, and claims priority based on provisional application Ser. No. 61/067,403, filed Feb. 28, 2008, the contents of which are incorporated by reference in their entireties.

This invention relates to the production of ethanol. More particularly, this invention relates to the production of ethanol from methanol.

This invention also relates to the production of ethanol from syngas. The syngas may be produced by gasifying biomass. A portion of the carbon monoxide and a portion of the hydrogen contained in the syngas are reacted to produce methanol. The methanol is reacted with carbon monoxide from the syngas to produce methyl acetate, which is reacted with hydrogen, also from the syngas, to produce ethanol.

Ethanol is a fuel that is used primarily as a gasoline additive. Blends of ethanol and gasoline, containing between 5% and 85% ethanol, have been commercialized. Ethanol has a higher octane number than gasoline, and it is combusted completely in spark-ignited internal combustion engines. Because ethanol can be derived from renewable biomass, its use in blends of ethanol and gasoline contributes to the reduction of greenhouse gas emissions in the transportation sector.

U.S. published Patent Application No. 2007/0270511 discloses the production of synthesis gas, or syngas, from biomass. The synthesis gas then is reacted in the presence of a catalyst to produce a reaction product that includes methanol, carbon monoxide, and hydrogen. The methanol, carbon monoxide, and hydrogen are reacted in a carbonylation reactor in the presence of a carbonylation catalyst to produce methyl acetate, as well as acetic acid and water. The acetic acid then may be reacted with ethanol to produce ethyl acetate. The methyl acetate and ethyl acetate then are hydrogenated in the presence of a hydrogenation catalyst to produce ethanol.

In this application, hydrogen is not separated from the synthesis gas prior to the reaction of methanol with carbon monoxide. Because a significant amount of hydrogen is present along with the methanol and carbon monoxide in the carbonylation reactor, the carbonylation of the methanol with carbon monoxide is hindered significantly.

In accordance with an aspect of the present invention, there is provided a process for converting methanol to ethanol. The process comprises reacting methanol and carbon monoxide (such as, for example, a carbon monoxide-rich gas derived from syngas) under conditions to produce a product comprising at least 25 mole % methyl acetate. The methyl acetate then is hydrogenolyzed and hydrogenated using hydrogen (such as, for example, hydrogen which has been separated from syngas) to produce ethanol.

In accordance with one non-limiting embodiment, syngas is produced in order to provide all or a portion of the methanol, hydrogen, and CO requirements for the process.

The reaction of methanol and carbon monoxide is a carbonylation reaction, which creates a carbon-carbon (C—C) bond, and which may be effected in the presence of a catalyst, which, under appropriate conditions, provides acetic acid and/or methyl acetate. If the reaction of methanol and carbon monoxide is conducted under conditions having a sufficient molar ratio of methanol to carbon monoxide, i.e., a sufficient molar excess of methanol vis-à-vis carbon monoxide, and a sufficient acidity, at least a portion of the formed acetic acid, via catalytic carbonylation, may be esterified rapidly to methyl acetate, thereby producing a reaction product that includes at least 25 mole % methyl acetate. The molar ratio of methyl acetate to acetic acid in the reaction product is a result of the kinetic rate of the acid catalysis following the carbonylation reaction, and it is limited by the equilibrium between the reactants and products. The equilibrium between reactants and products may be altered by changing reaction conditions such as temperature, pressure, and composition of reactants.

In a non-limiting embodiment, the methanol and carbon monoxide are reacted at a molar ratio of methanol to carbon monoxide of from about 2 to about 10. In another non-limiting embodiment, the methanol and carbon monoxide are reacted at a molar ratio of from about 2 to about 5.

In a non-limiting embodiment, the reaction product includes methyl acetate in an amount of at least 50 mole %. In another non-limiting embodiment, the reaction product includes methyl acetate in an amount greater than 75 mole %. In yet another non-limiting embodiment, the remaining component of the reaction product is essentially acetic acid.

In another non-limiting embodiment, the methanol and carbon monoxide are reacted at a temperature of from about 100° C. to about 350° C.

In another non-limiting embodiment, the methanol and carbon monoxide are reacted at a temperature of from about 120° C. to about 280° C. In another non-limiting embodiment, the methanol and carbon monoxide are reacted at a temperature of from about 150° C. to about 250° C. In a further non-limiting embodiment, the methanol and carbon monoxide are reacted at a temperature of from about 150° C. to about 200° C.

In another non-limiting embodiment, the methanol and carbon monoxide are reacted at a pressure of from about 15 atm to about 100 atm. In another non-limiting embodiment, the methanol and carbon monoxide are reacted at a pressure of from about 15 atm to about 50 atm. In yet another non-limiting embodiment, the methanol and carbon monoxide are reacted at a pressure of from about 20 atm to about 50 atm.

In one non-limiting embodiment, the reaction of methanol with carbon monoxide is effected by reacting methanol with a syngas, such as a CO-rich syngas.

The methanol and carbon monoxide are reacted in the presence of a suitable catalyst for converting methanol and carbon monoxide to acetic acid and methyl acetate. The reaction of methanol with carbon monoxide may be effected in the liquid phase or in the gas phase.

In a non-limiting embodiment, such reaction (carbonylation plus acid catalysis) is effected in the liquid phase. In this case, the reaction, in a non-limiting embodiment, is effected catalytically in the presence of salts of active metals, or in the presence of finely divided and slurried powdered active metals. Such active metals include, but are not limited to, Group VIII metals such as Co, Ni, Pd, Ru, Rh, Re, Os, Ir, and the like. In a non-limiting embodiment, the active metal may be supported on an appropriate support including, but not limited to, carbon, alumina, silica, chromite, zirconia, or other stable oxides such as iron oxide, molybdenum oxide, and the like. The active metal may be employed in combination with a promoter such as a halide (e.g., bromide, chloride, iodide). In one non-limiting embodiment, the halide is an organic halide, such as a methyl halide. Alternatively, the halide is a metal halide. In another non-limiting embodiment, the promoter is a "green promoter," such as, for example, a dimethyl carbonate promoter. In another non-limiting embodiment, the active metal may be employed in combination with other additives, such as alkali metals (e.g., Li, Na, K, Rb, Cs), alkaline earth metals (e.g., Ba, Mg, Ca, Sr, Ra), and/or promoter metals such as Mo, Cu, Au, Ag, W, V, Cd, Cr, Zn, Mn, or Sn. The metals may be added to the liquid mixture as soluble inorganic salts, soluble organometallic compounds, or coordination complexes with carbonyls, for example. In an alternative non-limiting embodiment, the metals are added as finely divided powders which then are slurried in the reaction mixture.

In a non-limiting embodiment, the catalyst is suspended or dispersed in an inert liquid medium, such as, for example, an inert oil.

In another non-limiting embodiment, the catalyst is rhodium supported on carbon or alumina. The supported catalyst, in a non-limiting embodiment, is formed by impregnating the support with a non-halide rhodium salt. In an alternative non-limiting embodiment, the catalyst is formed by impregnating the support with rhodium and an alkali salt, such as a sodium salt, for example. After impregnation, the supported catalyst is calcined. In yet another non-limiting embodiment, the supported catalyst is suspended in an inert liquid, such as, for example, an inert oil such as Drakeol.

In yet another non-limiting embodiment, the reaction of methanol with carbon monoxide is effected in the gas phase. When the reaction is effected in the gas phase, the reaction, in a non-limiting embodiment, is effected in the presence of a catalyst, which may be a solid catalyst. Suitable catalysts include, but are not limited to, supported heterogeneous metals on matrices such as activated carbon, silica, alumina, chromite, zirconia, and other stable oxides at reaction conditions, such as iron oxide, molybdenum oxide, and the like. In another non-limiting embodiment, the catalyst is a sulfided catalyst, such as sulfided Co or sulfided Mo.

In another non-limiting embodiment, the support is an acidic support, such as an alumina support.

Metal catalysts which may be employed include, but are not limited to, the metals which may be employed in carrying out the reaction in the liquid phase.

As noted hereinabove, depending upon the conditions under which the methanol is reacted with the carbon monoxide, acetic acid may be present in the reaction product produced as a result of reacting the methanol and carbon monoxide. Thus, in another non-limiting embodiment, methanol and carbon monoxide are reacted under conditions to produce a product comprising at least 25 mole % methyl acetate and the remainder of the reaction product is essentially acetic acid. The acetic acid is reacted with at least one alcohol to produce at least one acetate. Thereafter, the "initial" methyl acetate, i.e., the methyl acetate produced as a result of reacting methanol with carbon monoxide, and the at least one acetate produced by reacting the acetic acid with the at least one alcohol, are hydrogenolyzed and hydrogenated to produce ethanol. As used herein, the term "hydrogenolysis" means the rupture of the ester bond in the presence of hydrogen, and the term "hydrogenation" means the addition of hydrogen to the moieties produced by the hydrogenolysis.

In another non-limiting embodiment, the acetic acid, when produced by reacting carbon monoxide with methanol as hereinabove described, is reacted with the at least one alcohol at a temperature of from about 80° C. to about 250° C. In another non-limiting embodiment, the acetic acid is reacted with the at least one alcohol at a temperature of from about 80° C. to about 150° C. In a further non-limiting embodiment, the acetic acid is reacted with the at least one alcohol at a temperature of from about 80° C. to about 120° C.

In yet another non-limiting embodiment, the acetic acid is reacted with the at least one alcohol at a pressure of from about 1 atm to about 20 atm. In a further non-limiting embodiment, the acetic acid is reacted with the at least one alcohol at a pressure of from about 1 atm to about 10 atm.

In a non-limiting embodiment, the at least one alcohol has 1 to 6 carbon atoms. In another non-limiting embodiment, the at least one alcohol is ethanol, and ethyl acetate is produced by reacting the acetic acid with ethanol. In another non-limiting embodiment, the at least one alcohol is methanol, and methyl acetate is produced by reacting the acetic acid with methanol. In another non-limiting embodiment, the at least one alcohol is butanol, and butyl acetate is produced by reacting the acetic acid with butanol. In yet another non-limiting embodiment, the acetic acid is reacted with methanol and ethanol to produce methyl acetate and ethyl acetate. In still another non-limiting embodiment, the acetic acid is reacted with methanol and butanol to produce methyl acetate and butyl acetate. In a further non-limiting embodiment, the acetic acid is reacted with methanol, ethanol, and butanol to produce methyl acetate, ethyl acetate, and butyl acetate.

In yet another non-limiting embodiment, the acetic acid and the at least one alcohol are reacted in the liquid phase (maintained by a suitable choice of temperature and pressure) in the presence of a suitable catalyst. Such catalysts include, but are not limited to, protonated zeolite catalysts, sulfuric acid, phosphoric acid, and protonated ionic exchange resins.

In another non-limiting embodiment, the acetic acid and the at least one alcohol are reacted in the gas phase in the presence of a suitable solid catalyst. Suitable catalysts include, but are not limited to, alumina, silica-alumina, protonated zeolites, and protonated ionic exchange resins.

In another non-limiting embodiment, the methyl acetate produced by reacting methanol and carbon monoxide (i.e., the "initial methyl acetate"), and, in cases where acetic acid also was produced by reacting methanol and carbon monoxide, the at least one acetate produced by reacting acetic acid with at least one alcohol, are reacted with the hydrogen at a temperature of from about 150° C. to about 300° C. to produce a reaction product which includes ethanol. In another non-limiting embodiment, the initial methyl acetate and the at least one acetate (if produced) are reacted with the hydrogen at a temperature of from about 170° C. to about 275° C. In yet another non-limiting embodiment, the initial methyl acetate and the at least one acetate (if produced) are reacted with the hydrogen at a temperature of from about 225° C. to about 275° C.

In yet another non-limiting embodiment, the initial methyl acetate and the at least one acetate (if produced) are reacted with hydrogen at a pressure of from about 10 atm to about 100 atm. In a further non-limiting embodiment, the initial methyl acetate and the at least one acetate (if produced) are reacted with the hydrogen at a pressure of from about 20 atm to about 60 atm.

In another non-limiting embodiment, the initial methyl acetate and the at least one acetate (if produced) are reacted with hydrogen at a molar ratio of hydrogen to acetate of at least 3. In another non-limiting embodiment, the initial methyl acetate and the at least one acetate (if produced) are reacted with hydrogen at a molar ratio of hydrogen to acetate of from about 5 to about 10.

In one non-limiting embodiment, the reaction of the initial methyl acetate and the at least one acetate (if produced) with hydrogen is effected by reacting the initial methyl acetate and the at least one acetate (if produced) with a syngas, such as an $H_2$-rich syngas.

In another non-limiting embodiment, the initial methyl acetate and the at least one acetate (if produced) are reacted with hydrogen in the presence of a hydrogenation catalyst. Representative examples of hydrogenation catalysts which may be employed include, but are not limited to, $Cu/Cr_2O_3$, $Cu/ZnO/Al_2O_3$, $Cu/Al_2O_3$, $Cu/ZnO$/carbon, $Cu$/carbon, and combinations of $Cu/Zn/Fe$ and $Cu/Zn/Fe/Co$ on appropriate catalyst supports.

In another non-limiting embodiment, one or both of the carbon monoxide and hydrogen that are employed in the process of the present invention is obtained from synthesis gas, or syngas. In yet another non-limiting embodiment, each of the carbon monoxide and hydrogen is obtained from syngas. In a further non-limiting embodiment, a portion of the carbon monoxide and a portion of the hydrogen obtained from the syngas are reacted to produce methanol, which is employed in the process of the present invention.

Thus, in accordance with another aspect of the present invention, there is provided a process for producing ethanol from synthesis gas. The synthesis gas comprises carbon monoxide and hydrogen, and may be produced by methods known to those skilled in the art, such as, for example, those disclosed in PCT Application No. WO00/69994. A portion of the carbon monoxide and a portion of the hydrogen from the synthesis gas are reacted to produce methanol. The methanol then is reacted with another portion of the carbon monoxide from the syngas, under conditions hereinabove described, to produce a product comprising at least 25 mole % methyl acetate. As noted hereinabove, the product may further include acetic acid. If acetic acid is present in the product, such acetic acid is reacted with at least one alcohol under conditions hereinabove described to product at least one acetate. The methyl acetate produced by reacting methanol with carbon monoxide (i.e., the "initial methyl acetate"), and the at least one acetate (if present) formed by reacting acetic acid with at least one alcohol, then are hydrogenated with another portion of the hydrogen from the syngas, under conditions hereinabove described, to produce ethanol.

In a non-limiting embodiment, the syngas is obtained by gasifying carbonaceous materials such as polyethylene and polypropylene residues, rubber residues, and biomass such as biological treatment sludge, forest biomass, agricultural biomass, and urban biomass. Examples of the gasification of such carbonaceous materials are disclosed in PCT Application No. WO00/69994, the contents of which are incorporated herein by reference. When urban biomass is employed, such urban biomass may be obtained from municipal solid waste following sorting, drying (biologically or thermally using low grade heat from the gasification process), and size reduction. The crude synthesis gas produced by the gasification of biomass is conditioned such that impurities are reduced to a level that permits the catalytic synthesis of methanol wherein said catalyst may be on stream for at least 5,000 hours before regeneration. In a non-limiting embodiment, the methanol synthesis is effected at a $H_2$:CO ratio of from about 1:1 to about 3:1.

In another non-limiting embodiment, the methanol synthesis is effected under conditions such that CO is converted to methanol at a rate of up to 50 mole %. The unconverted syngas then is separated from the methanol and passed through a membrane whereby the syngas is fractionated into a CO-rich portion and a hydrogen-rich portion. In a non-limiting embodiment, the syngas is passed through a commercially available hollow-fiber membrane. Examples of hollow-fiber membranes which may be employed include, but are not limited to, PRISM™, POLYSEP™ VAPORSEP™, or other separation systems which provide for a permeate rich in $H_2$ and a retentate rich in CO. In another non-limiting embodiment, the syngas is passed through the membrane at a temperature which does not exceed 150° C., and at a pressure which does not exceed 30 atm.

Hydrogen permeates the membrane while a CO-rich gas does not permeate the membrane. The CO-rich gas, which does not pass through the membrane, may contain $CO_2$ in an amount that does not exceed 15 mole %, and hydrogen in an amount that does not exceed 5 mole %. Such CO-rich gas is reacted with methanol under conditions to provide a product comprising methyl acetate in an amount of at least 25 mole %. Acetic acid also may be produced.

The recovered pure hydrogen, which permeates the membrane, may be used downstream for the hydrogenolysis/hydrogenation of methyl acetate produced as a result of the reaction of methanol with carbon monoxide. If, in addition to methyl acetate, the reaction of methanol with carbon monoxide also produces acetic acid, the acetic acid is reacted with at least one alcohol to produce at least one acetate. Such at least one acetate and the initial methyl acetate are reacted with the recovered pure hydrogen to produce ethanol.

In another non-limiting embodiment, the syngas, which has been conditioned to have a $H_2$:CO molar ratio of from 1:1 to 3:1, and includes $CO_2$ in an amount which does not exceed 15 mole %, methane in an amount that does not exceed 5 mole %, and water vapor in an amount that does not exceed 5 mole %, is reacted in the presence of a methanol synthesis catalyst, such as, for example, a $Cu/ZuO/Al_2O_3$ catalyst dispersed in an inert oil to provide methanol, as well as residual carbon monoxide and hydrogen.

The methanol then is reacted with the residual carbon monoxide from the syngas. In one embodiment, the residual carbon monoxide and hydrogen from the syngas, are passed through a series of selective membranes such as those hereinabove described, in order to provide a hydrogen-rich portion and a carbon-monoxide-rich portion, as hereinabove described. The carbon-monoxide-rich portion then is reacted with the methanol in the presence of a catalyst, to produce a product comprising methyl acetate (i.e., the "initial methyl acetate") in an amount of at least 25 mole % and also may produce acetic acid. In a non-limiting embodiment, the methanol and carbon monoxide are reacted in a liquid phase reactor. The methanol is reacted with the carbon monoxide at a temperature of from about 150° C. to about 200° C., and a pressure of from about 15 atm to about 50 atm.

The acetic acid (if produced) then is esterified to ethyl acetate and/or methyl acetate and/or butyl acetate by reacting the acetic acid with methanol and/or ethanol and/or butanol in the presence of an acid catalyst, such as those hereinabove described. The acetic acid is reacted with the methanol and/or ethanol and/or butanol at a temperature of from about 80° C. to about 250° C., and a pressure of from about 1 atm to about 20 atm. When reacted with ethanol, the acetic acid is converted to ethyl acetate. When reacted with methanol, the acetic acid is converted to methyl acetate. When reacted with butanol, the acetic acid is converted to butyl acetate.

The at least one acetate (if produced), which may be ethyl acetate, methyl acetate, or butyl acetate, or a combination of methyl acetate and/or ethyl acetate and/or butyl acetate, and the initial methyl acetate then are reacted with the residual hydrogen, recovered from the separation of carbon monoxide and hydrogen from the syngas, in the presence of a hydrogenation catalyst to produce ethanol, as well as methanol. When the at least one acetate (when produced) is butyl acetate, or a combination of methyl acetate and butyl acetate, butanol also is produced. The initial methyl acetate and the at least one acetate (if present) are reacted with hydrogen at a temperature of from about 150° C. to about 300° C. and at a pressure of from about 10 atm to about 100 atm.

The methanol that is produced as a result of reacting the methyl acetate with hydrogen, in a non-limiting embodiment, is recycled such that it is reacted with the carbon monoxide obtained from the syngas to provide a reaction product comprising at least 25 mole % methyl acetate. In another non-limiting embodiment, when acetic acid is included in such reaction product, a portion of the methanol also is recycled such that it is reacted with the acetic acid to produce methyl acetate. Likewise, in non-limiting embodiments, a portion of the ethanol, and/or butanol (when produced), may be recycled such that they are reacted with acetic acid to produce ethyl acetate and/or butyl acetate.

As noted hereinabove, methanol that is produced as a result of reacting methyl acetate with hydrogen can be recycled such that it is reacted with the carbon monoxide obtained from the syngas to provide methyl acetate, and with acetic acid when acetic acid also is produced, also to provide methyl acetate. Thus, in a non-limiting embodiment of the process of the present invention, the conversion of acetic acid to methyl acetate may be effected by use of an initial "start-up" quantity of methanol that is produced by reacting a portion of the hydrogen in the syngas to produce methanol. A portion of the methanol is reacted as hereinabove described to convert acetic acid to methyl acetate, which is hydrogenated to produce methanol and ethanol. The methanol thus produced, then is recycled and supplies the portion of methanol requirements for converting acetic acid to methyl acetate either during reaction between methanol and CO or in a separate step for converting acetic acid to methyl acetate.

Thus, in one non-limiting embodiment, the present invention provides a method of producing ethanol from biomass. Such method is effected by gasifying the biomass to produce syngas, which includes carbon monoxide and hydrogen. The carbon monoxide and hydrogen in the syngas are reacted to produce methanol. Unconverted syngas then is separated from the methanol and fractionated into a CO-rich portion and a hydrogen-rich portion. The CO-rich portion then is reacted with the methanol to produce a product comprising at least 25 mole % methyl acetate, and, in some cases, acetic acid. The methyl acetate then is reacted with the hydrogen-rich portion of the syngas to produce ethanol and methanol. The methanol produced in this reaction is recycled to be reacted with the CO-rich portion of the syngas to produce methyl acetate, or, when any acetic acid is produced, may be reacted with such acetic acid to produce additional methyl acetate, which then is reacted with the hydrogen-rich portion of the syngas to produce ethanol and methanol.

The invention now will be described with respect to the following examples; it is to be understood, however, that the scope of the present invention is not intended to be limited thereby.

EXAMPLE 1

The carbonylation of methanol with carbon monoxide is carried out in the liquid phase using a custom made (250 mL internal volume) SS 316 autoclave. The autoclave is heated with a salt bath (a eutectic mixture of nitrates and nitrites) whose temperature is controlled by an electrical heating system. Uniform temperature is maintained in the autoclave walls by the salt bath. Agitation of the liquid in the autoclave is made by a sparger-dispersor through which mixtures of gas ($N_2$, pure CO or CO-rich syngas) and vapors (of the volatile organics) are blown into the autoclave and bubbled through the liquid. The dispersor produces fine bubbles which maintain homogeneous agitation inside the liquid phase. The ensemble acts as a mini-bubbling column reactor. The autoclave has an exit port that sends the gas/vapor mixture to a reflux condenser operating at the same pressure as the autoclave. The reflux condenser is thermostated by a fluid circulating through a jacket and an internal coil. After the reflux condenser there is a backpressure regulator system that allows the pressure to drop to a desired level (1-40 atm). A final condensing system coupled with a chilled fluid (<15° C.) allows the condensed vapors to be recovered. The uncondensed gas is collected in a Teflon bag (initially purged) and analyzed. The initial charge, which occupies ⅔ of the autoclave internal volume is comprised of $RhCl_3.3H_2O$ or $RhI_3$ (in both cases the Rh concentration is in the range from 3 to $5\times10^{-3}$ M), iodide salt (LiI and NaI are used at 0.5-0.75 M), water (1.0-5.0 M) and acetic acid (its molar concentration accounts for the difference). The autoclave is flashed repeatedly with $N_2$ prior to and after introducing the charge. Thus at time zero the autoclave has the charge plus inert $N_2$ at a pressure slightly above atmospheric. The autoclave then is heated to reaction temperature which is varied from 170 to 200 C. Methanol, methyl iodide, and methyl acetate are pumped via independent pumping systems (with refrigerated heads) into a thermostated (<15° C.) static mixing system. Methyl acetate is added at molar ratios relative to methanol that do not exceed 1:10. Methyl iodide is added to maintain an iodide concentration in the liquid phase ranging from 0.1 to 2.0 M. From the static mixing system the uniform liquid mixture is sent to a small reservoir from where it is pumped under pressure through a heat exchanger. The vaporized mixture is directed to a second static mixer where it mixes with the reactive gas (CO-rich gas ranging from pure CO to a mixture of CO as the main gas with $CO_2$, up to 10 vol. %, light hydrocarbons up to 10 vol. %, and hydrogen, up to 2 vol. %). The pressure can be controlled so that the pressure in the autoclave is between 20 and 50 atm. The temperature is varied from 170 to 200° C. The gas/vapor mixture moves into the autoclave through an appropriate valving system and bubbles through the liquid. The controlled flow rate dictates the hourly space velocities which range between 10 and 100 mole MeOH liter$^{-1}$ h$^{-1}$. The CO used in these experiments is present at a molar ratio with respect to MeOH that ranges from 0.1 to 0.5 because the desired product is the acetate and not the acetic acid. CO is converted to a mixture of methyl acetate and acetic acid (molar ratio of 3:1, methyl acetate to acetic acid). The acetic acid can be converted further to the acetate in a separate reactor.

EXAMPLE 2

The carbonylation of methanol with carbon monoxide is carried out in the liquid phase using the custom made (250 mL internal volume) SS 316 autoclave described in the preceding example. The autoclave is heated with a salt bath (a eutectic mixture of nitrates and nitrites) whose temperature is controlled by an electrical heating system. Uniform temperature is maintained in the autoclave walls by the salt bath. Agitation of the liquid in the autoclave is made by a sparger-dispersor through which mixtures of gas ($N_2$, pure CO or CO-rich syngas) and vapors (of the volatile organics) are blown into the autoclave and bubbled through the liquid. The disperser produces fine bubbles which maintain homogeneous agitation inside the liquid phase. The ensemble acts as a mini-bubbling column reactor. The autoclave has an exit port that sends the gas/vapor mixture to a reflux condenser operating at the same pressure as the autoclave. The reflux condenser is thermostated by a fluid circulating through a jacket and an internal coil. After the reflux condenser there is a backpressure regulator system that allows the pressure to drop to a desired level (1-40 atm). A final condensing system coupled with a chilled fluid (<15° C.) allows the condensed vapors to be recovered. The uncondensed gas is collected in a Teflon bag (initially purged) and analyzed. The initial charge, which occupies ⅔ of the autoclave internal volume is comprised of soluble non-halide Rh salts (the Rh concentration is in the range from 3 to $5 \times 10^{-3}$ M), carbonate salts (Li and Na are used at 0.5-0.75 M), water (1.0-5.0 M) and acetic acid (its molar concentration accounts for the difference). The autoclave is flashed repeatedly with $N_2$ prior to and after introducing the charge. Thus at time zero the autoclave has the charge plus inert $N_2$ at a pressure slightly above atmospheric. The autoclave then is heated to reaction temperature which is varied from 170° to 200° C. Methanol, dimethyl carbonate (which can be obtained by reacting produced methanol and separated carbon dioxide in a separate reactor), and methyl acetate are pumped via independent pumping systems (with refrigerated heads) into a thermostated (<15° C.) static mixing system. Methyl acetate is added at molar ratios relative to methanol that do not exceed 1:10. Dimethyl carbonate is added to maintain a carbonate concentration in the liquid phase ranging from 0.1 to 2.0 M. From the static mixing system the uniform liquid mixture is sent to a small reservoir from where it is pumped under pressure through a heat exchanger. The vaporized mixture is directed to a second static mixer where it mixes with the reactive gas (CO-rich gas ranging from pure CO to a mixture of CO as the main gas with $CO_2$, up to 10 vol. %, light hydrocarbons up to 10 vol. %, and hydrogen, up to 2 vol. %). The pressure can be controlled so that the pressure in the autoclave is between 20 and 50 atm. The temperature is varied from 17° to 200° C. The gas/vapor mixture moves into the autoclave through an appropriate valving system and bubbles through the liquid. The controlled flow rate dictates the hourly space velocities which range between 10 and 100 mole MeOH liter$^{-1}$ h$^{-1}$. The CO used in these experiments is present at a molar ratio with respect to MeOH that ranges from 0.1 to 0.5 because the desired product is the acetate and not the acetic acid. CO is converted to a mixture of methyl acetate and acetic acid (molar ratio of 3:1, methyl acetate to acetic acid). The acetic acid can be converted further to the acetate in a separate reactor.

EXAMPLE 3

A gas/vapor set of experiments is carried out using a fixed bed reactor in which two types of catalysts are tested: Rh on carbon and on alumina, and Ir also on both carbon and alumina. Impregnation of the supports is made to provide 0.5-1.0 wt % of metal on the support. The supports also are impregnated with alkali or alkali iodide at molar ratios of 2 to 5 with respect to the metal impregnated previously. Calcination followed at 350° C. The reactor was an SS 316 15.875 mm internal diameter (i.d.) reactor lined with a thin (1 mm) sheet of pure copper. The catalyst is placed between two zones filled with carborundum grains (previously deionized). The catalyst bed has a length of 25 cm and the catalyst is mixed on a 50/50 wt basis with the same carborundum used in the upper and lower zones holding the catalyst zone. Methanol and pure CO or CO-rich syngas of the same composition shown in Example 1 are added as a vapor/gas mixture prepared by the same system also described in Example 1. The methanol to CO molar ratio is between 1 and 5, whereas the methyl iodide added to the methanol is maintained at a molar ratio between 0.05 and 0.25, relative to the methanol. Reaction conditions are such that the GHSV, based on CO passed through the catalytic bed, varies between 2000 and 10000 h$^{-1}$. After being blown through the catalytic bed at a temperature from 175 to 300° C., and a pressure from 10 to 50 atm, it is found that the CO is converted at a rate near 100% when the methanol:CO molar ratio is >2. The selectivity varies as a function of temperature and pressure. It is found that within a wide range (200-240° C., 15-50 atm) for the specified GHSV range one obtains a molar selectivity of 50-75% acetate and 25-50% acetic acid.

EXAMPLE 4

A second gas/vapor set of experiments is carried out using a fixed bed reactor in which the two types of catalysts above described are tested: Rh on carbon and on alumina, and Ir also on both carbon and alumina. Impregnation of the supports is made from non-halide salts to provide 0.5-1.0 wt % of metal on the support. The supports also are impregnated with alkali at molar ratios of 2 to 5 with respect to the metal impregnated previously. Calcination followed at 350° C. The reactor was an SS 316 15.875 mm internal diameter (i.d.) reactor lined with a thin (1 mm) sheet of pure copper. The catalyst is placed between two zones filled with carborundum grains (previously deionized). The catalyst bed has a length of 25 cm and the catalyst is mixed on a 50/50 wt basis with the same carborundum used in the upper and lower zones holding the catalyst zone. Methanol and pure CO or CO-rich syngas of the same composition shown in Example 1 are added as a vapor/gas mixture prepared by the same system also described in Example 1. The methanol to CO molar ratio is between 1 and 5, whereas the dimethyl carbonate (which can be obtained by reacting produced methanol and separated carbon dioxide in a separate reactor) added to the methanol is maintained at a molar ratio between 0.05 and 0.25, relative to the methanol. Reaction conditions are such that the GHSV, based on CO passed through the catalytic bed, varies between 2,000 and 10,000 h$^{-1}$. After being blown through the catalytic bed at a temperature from 175 to 300° C., and a pressure from 10 to 50 atm, it is found that the CO is converted at a rate near 100% when the methanol:CO molar ratio is greater than 2. The selectivity varies as a function of temperature and pressure. It is found that within a wide range (200-240° C., 15-50 atm) for the specified GHSV range one obtains a molar selectivity of 50-75% acetate and 25-50% acetic acid.

EXAMPLE 5

Acetic acid (1500 mL or 25 gmoles) produced in accordance with Examples 1 or 3, in liquid form is placed in a 5000 mL vessel acting as a reboiler. Above the vessel there is an insulated packed distillation column (acting as an enriching section). The top of the distillation column is linked to a reflux condenser that is operated at a temperature of about 70° C. The vessel is heated externally to a temperature of from 95° C. to 105° C. at a pressure of 1 atm. Phosphoric acid is added to the acetic acid in an amount of from 1 wt % to 5 wt %, of the weight of the acetic acid. Ethanol, placed in a 2000 mL vessel, is entrained by bubbling nitrogen through the vessel, which is maintained at a temperature not exceeding 50° C. The nitrogen-entrained alcohol is bubbled through the acetic acid/phosphoric acid mixture. Bubbling rates are adjusted in the 0.01-10 mole alcohol/min range. Bubbling is facilitated by a diffuser. Reflux is generated internally by the condensed liquid. The column has a packing height that is from 0.2 to 0.5 m. The operation is carried out in such mode that an azeotrope mixture (composition verified by chromatography) of 83 mole % ethyl acetate, 9 mole % ethanol and 5 mole % water vapor leaves the condenser at 70° C. and is subjected to cooling to 20° C. Two phases then are obtained: an upper organic phase and a bottom phase containing most of the water and ethanol. The organic phase is redistilled to produce a small amount of azeotrope (light phase) and essentially pure ethyl acetate (heavy phase). The conversion of incoming ethanol is dictated by the azeotrope equilibrium limit, essentially 90% within a wide range of contact times (corresponding to the different bubbling rates). Unconverted ethanol, dissolved with water in the bottom phase obtained after cooling to 20° C., is dehydrated and recycled to the system. The small amount of azeotrope resulting from the second distillation is returned to the system as such.

EXAMPLE 6

A mixture of methanol and acetic acid, produced in accordance with Example 1 or Example 3, having a molar ratio of 1:5 (methanol to acetic acid) is pumped through a heat exchanger that vaporizes the totality of the liquid at 1 atm using a shell and tube heat exchanger which brings the mixture temperature in the range of 125 to 175° C. A small amount of nitrogen also is bled into the heat exchanger. The heated $N_2$ and vapor mixture, containing less than 10 vol. % $N_2$, then is blown through a catalytic bed containing either alumina or a protonated zeolite of a suitable pore diameter. The LHSV (liquid hourly space velocity, defined as liters/h of liquid mixture at 25° C. passed through a given volume, in liters of packed catalyst) is between 1 and 5 $h^{-1}$. The fixed bed reactor is maintained at isothermal conditions within the range of 125 to 175° C. The vapors leaving the reactor are condensed at 25° C. and cooled further to less than 15° C. Samples of the liquid thus recovered are analyzed chromatographically. Only traces of methanol are found. The methanol is converted totally to methyl acetate within the range of conditions used.

EXAMPLE 7

The reaction of Example 6 is carried out as hereinabove described except that the molar ratio of methanol to acetic acid is 5:1. The product contains no acetic acid. Methanol, methyl acetate (corresponding to full conversion of the acetic acid) and water are the only products detected at measurable levels.

EXAMPLE 8

Methyl acetate produced in accordance with Examples 6 or 7, and maintained as a liquid at 20° C., is pumped at a pressure from 10 to 50 atm, through a heat exchanger that vaporizes it completely at a temperature from 150 to 225° C. Preheated hydrogen at the same temperature range is added to the vapors at their exit from the heat exchanger. The molar ratio $H_2$ to methyl acetate is from 5 to 10. The hot mixture is blown through a catalytic bed where a $CuO/Cr_2O_3$, a $CuO/ZnO/Al_2O_3$, or a CuO/ZnO/activated carbon catalyst are placed together with an inert solid which acts as diluent of the catalyst. The CuO is reduced with $H_2/N_2$ mixtures prior to adding any acetate. The CuO is thus reduced to Cu, the active form in the hydrogenolysis reaction. The reduction is carried out until no water is produced. The exothermicity of the reduction of the CuO is controlled by keeping the $H_2$ concentration in the gas mixture at levels not exceeding 5 vol. %. Liquid hourly space velocities (LHSV) are from 1 to 10 $h^{-1}$ relative to the methyl acetate flow rates and to the true volume occupied by the catalyst (with no inert solid present). The conversion of 1 mole of methyl acetate into 0.90 mole of methanol and 0.90 mole of ethanol is carried out within the ranges of operating parameters considered. The amount of unconverted methyl acetate is 0.10 mole.

EXAMPLE 9

Ethyl acetate, produced in accordance with Example 5, and maintained as a liquid at 20° C., is pumped at a pressure from 10 to 50 atm, through a heat exchanger that vaporizes it completely at a temperature from 150 to 225° C. Pretreated hydrogen in the same temperature range is added to the vapors at their exit from the heat exchanger. The molar ratio of $H_2$ to ethyl acetate is from 5 to 10. The hot mixture is blown through a three phase reactor where a powdered (0.1-0.5 mm) $CuO/ZnO/Al_2O_3$ or a CuO/ZnO/activated carbon solid catalyst is suspended (at 20 and 30 wt % solids) in an inert mineral oil. The CuO is reduced with $H_2/N_2$ mixtures prior to adding any acetate. The CuO is thus reduced to Cu, the active form in the hydrogenolysis reaction. The reduction is carried out until no water is produced. The exothermicity of the reduction of the CuO is controlled by keeping the $H_2$ concentration in the gas mixture at levels not exceeding 5 vol. %. Gas hourly space velocities (GHSV, at 15° C. and 1 atm) based on $H_2$, are between 1000 and 10000 $h^{-1}$. The conversion of 1 mole of ethyl acetate into 1.90 moles of ethanol is carried out within the ranges of operating parameters considered. The amount of unconverted ethyl acetate is 0.05 mole.

EXAMPLE 10

Methyl acetate is converted to methanol and ethanol as described in Example 8, or ethyl acetate is converted to ethanol as described in Example 9, except that the methyl acetate or ethyl acetate is reacted with syngas containing $H_2$, CO, $CO_2$, and light hydrocarbons such as methane. The molar ratio of $H_2$:CO is varied from 1 to 3. The $CO_2$ in the syngas does not exceed 10 mole %, and the light hydrocarbons in the syngas do not exceed 10 mole %. The total pressure is varied from 30 atm to 100 atm. 90 molar % conversion of methyl acetate to methanol and ethanol, and 95 molar % conversion of ethyl acetate to ethanol are observed.

EXAMPLE 11

A. Carbonylation of Methanol to Acetic Acid and Methyl Acetate

The carbonylation of methanol with carbon monoxide is carried out in the liquid phase using a custom made (250 mL internal volume) SS 316 autoclave into which a glass liner is placed. The internal diameter of the liner is 25 mm. The initial charge into the autoclave occupies between ½ and ⅔ of the autoclave's internal volume. The initial charge is comprised of an inert oil (Drakeol) and a finely divided (0.4-0.8 mm) dispersed solid catalyst (active metal on a solid support as described below). The Solid catalyst comprises between 20 and 30 wt % of the total mass (inert oil plus solids) charged. The autoclave is heated with a salt bath (a eutectic mixture of nitrates and nitrites) whose temperature is controlled by an electrical heating system. Uniform temperature is maintained in the autoclave walls by the salt bath. Agitation of the liquid in the autoclave is made by a sparger-dispersor through which mixtures of gas ($N_2$, pure CO or CO-rich syngas) and vapors (of the volatile organics) are blown into the autoclave and bubbled through the liquid. The dispersor produces fine bubbles which maintain homogeneous agitation inside the liquid phase. The ensemble acts as a mini-bubbling column reactor. The autoclave has an exit port that sends the gas/vapor mixture to a reflux condenser operating at the same pressure as the autoclave. The reflux condenser is thermostated (at 175° to 200° C.) by a fluid circulating through a jacket and an internal coil. After the reflux condenser there is a back pressure regulator, also thermostated at same temperatures as the reflux condenser, that allows the pressure to drop to a desired level (1-20 atm). A final condensing system coupled with a chilled fluid (<15° C.) allows the condensed vapors to be recovered. The uncondensed gas is collected, following a second back pressure regulator which lowers the pressure to slightly above atmospheric, in a Teflon bag (initially purged) and analyzed.

Two types of catalysts are employed: Rh on carbon and on alumina. The supports are impregnated with non-halide salts of rhodium to provide 0.5-1.0 wt % of rhodium on the support. The supported rhodium catalysts also were made with and without impregnation with alkali (Na) at molar ratios of 2 to 5 with respect to the rhodium. The supported rhodium catalysts then are calcined at 350° C.

The autoclave is flashed repeatedly with $N_2$ after introducing the oil plus catalyst charge. Thus at time zero the autoclave has the oil and catalyst charge plus inert $N_2$ at a pressure slightly above atmospheric. The autoclave then is heated to reaction temperature which is varied from 175° to 250° C. Methanol, methyl iodide or dimethyl carbonate (which can be obtained by reacting produced methanol and separated carbon dioxide in a separate reactor), and methyl acetate are pumped via independent pumping systems (with refrigerated heads) into a thermostated (<15° C.) static mixing system. Methyl acetate is added at molar ratios relative to methanol that do not exceed 1:10. Methyl acetate or dimethyl carbonate is added to maintain a carbonate concentration in the liquid phase ranging from 0.1 to 2.0 M. The liquids are mixed in a pressurized reservoir and the uniform mixed liquid mixture is pumped under pressure through a heat exchanger. The vaporized mixture is directed to a second static mixer where it mixes with the reactive gas (CO-rich gas ranging from pure CO to a mixture of gases with CO as the main gaseous component, and including up to 10 vol. % $CO_2$, up to 10 vol. % light hydrocarbons, up to 5 vol. % hydrogen). The pressure is controlled so that the pressure in the autoclave is between 20 and 50 atm. The temperature is varied from 175° to 250° C. The gas/vapor mixture is directed through a disperser into the autoclave, and bubbles through the inert oil/solid catalyst mixture, thereby forcing agitation and mixing. Temperature is controlled within 2° C. despite the exothermicity of the reaction. The controlled flow rate dictates the hourly space velocities which range between 10 and 100 mole methanol liter$^{-1}$ h$^{-1}$. The CO used in these experiments is present at a molar ratio with respect to methanol that ranges from 0.1 to 0.5 when the desired major product is the acetate and not acetic acid. CO is converted to mixtures of methyl acetate and acetic acid (molar ratio of 3:1, methyl acetate to acetic acid). When the CO to methanol molar ratio is above 1.5, the predominant product is acetic acid. The acetic acid can be converted further to the acetate in a separate reactor.

B. Esterification of the Acetic Acid

A mixture of methanol and acetic acid, produced as hereinabove described, and having a molar ratio of 1:5 (methanol to acetic acid) is pumped through a heat exchanger that vaporizes the totality of the liquid at 1 atm using a shell and tube heat exchanger which heats the mixture to a temperature in the range of 125° to 175° C. A small amount of nitrogen also is bled into the heat exchanger. The heated $N_2$ and vapor mixture, containing less than 10 vol. % $N_2$, then is blown through a catalytic bed containing alumina or a protonated zeolite having a suitable pore diameter as a catalyst, blended with a dehydration zeolite. The LHSV (liquid hourly space velocity, defined as liters/h of liquid mixture at 25° C. passed through a given volume, in liters, of packed catalyst) is between 1 and 5 h$^{-1}$. The fixed bed reactor is maintained at isothermal conditions within the range of 100° to 150° C. The vapors leaving the reactor are passed through a dehydration zeolite which eliminates traces of water. Then the vapors are condensed at 25° C. and cooled further to less than 15° C. Samples of the liquid thus recovered are analyzed chromatographically. Only traces of methanol are found. The methanol is converted totally to methyl acetate within the range of conditions used. The water-loaded dehydration zeolites are regenerated easily by heating.

The esterification reaction also can be carried out as hereinabove described except that the molar ratio of methanol to acetic acid is 5:1, thereby providing a product that contains no acetic acid. Methanol, methyl acetate (corresponding to full conversion of the acetic acid), and water are the only products detected at measurable levels.

Such "swing esterification" overcomes the inherent equilibrium limitations by removing the water formed. The dehydration agent also could be a temperature resistant (up to 175° C.) membrane, thus removing the water as it is produced. Tubular reactors having hollow fiber configurations thus could be implemented.

C. Hydrogenolysis of the Acetate

Methyl acetate produced as hereinabove described, and maintained as a liquid at 20° C., is pumped at a pressure from 10 to 50 atm, through a heat exchanger that vaporizes it completely at a temperature from 150° to 225° C. Preheated hydrogen at the same temperature range is added to the vapors as they exit from the heat exchanger. The molar ratio $H_2$ to methyl acetate is from 5 to 10. The hot mixture is blown through a catalytic bed including a $CuO/Cr_2O_3$, a $CuO/ZnO/Al_2O_3$, or a CuO/ZnO/activated carbon catalyst and an inert solid which acts as a diluent of the catalyst. The CuO is reduced to Cu by adding a mixture of $H_2$ and $N_2$ prior to adding any acetate. The CuO is thus reduced to Cu, the active form in the hydrogenolysis reaction. The reduction is carried out until no water is produced. The exothermicity of the reduction of the CuO is controlled by keeping the $H_2$ concentration in the gas mixture at levels not exceeding 5 vol. %. For the hydrogenolysis, the liquid hourly space velocities (LHSV) are from 1 to 10 h$^{-1}$ relative to the methyl acetate flow rates and to the true volume occupied by the catalyst (with no inert solid present). Temperature of the reactor is maintained from 225° to 275° C. The conversion of 1 mole of methyl acetate into 0.90 mole of methanol and 0.90 mole of ethanol is carried out within the above mentioned operating parameters. The unconverted methyl acetate, 0.10 mole, is separated from the methanol and ethanol products, and is saponified at room temperature with caustic on a stoichiometric basis. Sodium acetate is produced readily in a water solution. Using a bipolar membrane permits the recovery of the caustic (for recycling) and of the acetic acid which is recycled to the esterification reaction.

The disclosures of all patents and publications, including published patent applications, are hereby incorporated by reference to the same extent as if each patent or publication were individually and specifically incorporated by reference.

It is to be understood, however, that the scope of the present invention is not to be limited to the specific embodiments described above. The invention may be practiced other than as particularly described and still be within the scope of the accompanying claims.

What is claimed is:

1. A process for converting methanol to ethanol, comprising:
   (a) reacting methanol and carbon monoxide in the liquid phase, and under conditions to produce a product comprising at least 25 mole % methyl acetate; and
   (b) hydrogenating said methyl acetate to produce ethanol.

2. The process of claim 1 wherein said methanol and said carbon monoxide are reacted at a molar ratio of methanol to carbon monoxide of from about 2 to about 10.

3. The process of claim 2 wherein said methanol and said carbon monoxide are reacted at a molar ratio of methanol to carbon monoxide of from about 2 to about 5.

4. The process of claim 1 wherein said methanol and said carbon monoxide are reacted at a temperature of from about 100° C. to about 350° C.

5. The process of claim 4 wherein said methanol and said carbon monoxide are reacted at a temperature of from about 120° C. to about 280° C.

6. The process of claim 5 wherein said methanol and said carbon monoxide are reacted at a temperature of from about 150° C. to about 250° C.

7. The process of claim 6 wherein said methanol and said carbon monoxide are reacted at a temperature of from about 150° C. to about 200° C.

8. The process of claim 1 wherein said methanol and said carbon monoxide are reacted at a pressure of from about 15 atm to about 100 atm.

9. The process of claim 8 wherein said methanol and said carbon monoxide are reacted at a pressure of from about 15 atm to about 50 atm.

10. The process of claim 9 wherein said methanol and said carbon monoxide are reacted at a pressure of from about 20 atm to about 50 atm.

11. The process of claim 1 wherein said methanol and said carbon monoxide are reacted in the presence of a catalyst.

12. The process of claim 11 wherein said catalyst comprises rhodium.

13. The process of claim 12 wherein said catalyst comprises rhodium supported on a support selected from the group consisting of carbon and alumina.

14. The process of claim 11 wherein said catalyst is dispersed in an inert liquid medium.

15. The process of claim 14 wherein said inert liquid medium is an inert oil.

16. The process of claim 1 wherein, in step (a), said methanol is reacted with a CO-rich syngas.

17. The process of claim 1 wherein said product in step (a) further comprises acetic acid.

18. The process of claim 17, and further comprising:
    prior to step (b), reacting said acetic acid with at least one alcohol to produce at least one acetate, and in step (b), hydrogenating (i) said methyl acetate produced in step (a), and (ii) said at least one acetate produced by reacting said acetic acid with at said least one alcohol, to produce ethanol.

19. The process of claim 18 wherein said acetic acid is reacted with said at least one alcohol at a temperature of from about 80° C. to about 250° C.

20. The process of claim 19 wherein said acetic acid is reacted with said at least one alcohol at a temperature of from about 80° C. to about 150° C.

21. The process of claim 20 wherein said acetic acid is reacted with said at least one alcohol at a temperature of from about 80° C. to about 120° C.

22. The process of claim 18 wherein said acetic acid is reacted with said at least one alcohol at a pressure of from about 1 atm to about 20 atm.

23. The process of claim 22 wherein said acetic acid is reacted with said at least one alcohol at a pressure of from about 1 atm to about 10 atm.

24. The process of claim 18 wherein said at least one alcohol is ethanol.

25. The process of claim 18 wherein said at least one alcohol is methanol.

26. The process of claim 18 wherein said at least one alcohol is butanol.

27. The process of claim 18 wherein said at least one alcohol includes methanol and ethanol.

28. The process of claim 1 wherein said methyl acetate is hydrogenated at a temperature of from about 150° C. to about 300° C.

29. The process of claim 28 wherein said methyl acetate is hydrogenated at a temperature of from about 170° C. to about 275° C.

30. The process of claim 29 wherein said methyl acetate is hydrogenated at a temperature of from about 225° C. to about 275° C.

31. The process of claim 1 wherein said methyl acetate is reacted with said hydrogen at a pressure of from about 10 atm to about 100 atm.

32. The process of claim 31 wherein said methyl acetate is reacted with said hydrogen at a pressure of from about 20 atm to about 60 atm.

33. The process of claim 1, wherein, in step (b), said methyl acetate is hydrogenated by reacting said methyl acetate with a hydrogen-rich syngas.

34. A process for converting methanol to ethanol, comprising:
    (a) reacting methanol and carbon monoxide at a molar ratio of methanol to carbon monoxide of from about 2 to about 10, a temperature of from about 175° C. to about 250° C., and a pressure of from about 20 atm to about 50 atm, in the presence of a catalyst wherein said catalyst consists essentially of rhodium or consists essentially of rhodium supported on a support selected from the group consisting of carbon and alumina, wherein said catalyst is dispersed in an inert oil, to produce a product comprising at least 25 mole % methyl acetate; and
    (b) hydrogenating said methyl acetate at a molar ratio of hydrogen to methyl acetate of from about 5 to about 10, at a temperature of from about 225° C. to about 275° C., and at a pressure of from about 10 atm to about 50 atm, in the presence of a catalyst comprising copper, to produce ethanol.

35. A process for producing ethanol from synthesis gas, said synthesis gas comprising carbon monoxide and hydrogen, said process comprising:
    (a) reacting a first portion of said carbon monoxide with a first portion of said hydrogen to produce methanol;
    (b) reacting said methanol produced in step (a) with a second portion of said carbon monoxide in the liquid phase and under conditions to produce a product comprising at least 25 mole % methyl acetate; and
    (c) hydrogenating said methyl acetate with a second portion of said hydrogen to produce ethanol.

36. A process for producing ethanol from synthesis gas, said synthesis gas comprising carbon monoxide and hydrogen, said process comprising:
    (a) reacting said carbon monoxide of said synthesis gas with a first portion of said hydrogen of said synthesis gas to produce a product comprising methanol, wherein up to 50 mole % of said carbon monoxide is converted to said methanol;

(b) reacting said methanol produced in step (a) with the unreacted carbon monoxide from step (a) under conditions to produce a product comprising at least 25 mole % methyl acetate; and (c) hydrogenating said methyl acetate with a second portion of said hydrogen of said synthesis gas to produce ethanol.

37. The process of claim 36 wherein said first portion of said hydrogen is reacted with said carbon monoxide at a $H_2$:CO molar ratio of from about 1:1 to about 3:1.

38. The process of claim 36 wherein said methanol and said unreacted carbon monoxide from step (a) are reacted at a molar ratio of methanol to carbon monoxide of from about 2 to about 10.

39. The process of claim 38 wherein said methanol and said unreacted carbon monoxide from step (a) are reacted at a molar ratio of methanol to carbon monoxide of from about 2 to about 5.

40. The process of claim 36 wherein said methanol and said unreacted carbon monoxide from step (a) are reacted at a temperature of from about 100° C. to about 350° C.

41. The process of claim 40 wherein said methanol and said unreacted carbon monoxide from step (a) are reacted at a temperature of from about 120° C. to about 280° C.

42. The process of claim 41 wherein said methanol and said unreacted carbon monoxide from step (a) are reacted at a temperature of from about 150° C. to about 250° C.

43. The process of claim 42 wherein said methanol and said unreacted carbon monoxide from step (a) are reacted at a temperature of from about 150° C. to about 200° C.

44. The process of claim 36 wherein said methanol and said unreacted carbon monoxide from step (a) are reacted at a pressure of from about 15 atm to about 100 atm.

45. The process of claim 44 wherein said methanol and said unreacted carbon monoxide from step (a) are reacted at a pressure of from about 15 atm to about 50 atm.

46. The process of claim 45 wherein said methanol and said unreacted carbon monoxide from step (a) are reacted at a pressure of from about 20 atm to about 50 atm.

47. The process of claim 36 wherein said methanol and said unreacted carbon monoxide from step (a) are reacted in the presence of a catalyst.

48. The process of claim 47 wherein said catalyst comprises rhodium.

49. The process of claim 48 wherein said catalyst comprises rhodium supported on a support selected from the group consisting of carbon and alumina.

50. The process of claim 47 wherein said catalyst is dispersed in an inert liquid medium.

51. The process of claim 50 wherein said inert liquid medium is an inert oil.

52. The process of claim 36 wherein said product in step (a) further comprises acetic acid.

53. The process of claim 52, and further comprising: prior to step (b), reacting said acetic acid with at least one alcohol to produce at least one acetate, and in step (b), hydrogenating (i) said methyl acetate produced in step (a), and (ii) said at least one acetate produced by reacting said acetic acid with at least one alcohol, to produce ethanol.

54. The process of claim 53 wherein said acetic acid is reacted with said at least one alcohol at a temperature of from about 80° C. to about 250° C.

55. The process of claim 54 wherein said acetic acid is reacted with said at least one alcohol at a temperature of from about 80° C. to about 150° C.

56. The process of claim 55 where said acetic acid is reacted with said at least one alcohol at a temperature of from about 80° C. to about 120° C.

57. The process of claim 53 wherein said acetic acid is reacted with said at least one alcohol at a pressure of from about 1 atm to about 20 atm.

58. The process of claim 57 wherein said acetic acid is reacted with said at least one alcohol at a pressure of from about 1 atm to about 10 atm.

59. The process of claim 53 where said at least one alcohol is ethanol.

60. The process of claim 53 wherein said at least one alcohols is methanol.

61. The process of claim 53 wherein said at least one alcohol is butanol.

62. The process of claim 53 wherein said at least one alcohol includes methanol and ethanol.

63. The process of claim 36 wherein said methyl acetate is hydrogenated at a temperature of from about 150° C. to about 300° C.

64. The process of claim 63 wherein said methyl acetate is hydrogenated at a temperature of from about 170° C. to about 275° C.

65. The process of claim 64 wherein said methyl acetate is hydrogenated at a temperature of from about 225° C. to about 275° C.

66. The process of claim 36 wherein said methyl acetate is reacted with said hydrogen at a pressure of from about 10 atm to about 100 atm.

67. The process of claim 66 wherein said methyl acetate is reacted with said hydrogen at a pressure of from about 20 atm to about 60 atm.

68. A process for converting methanol to ethanol, comprising:

(a) reacting methanol and carbon monoxide in the presence of a catalyst, wherein said catalyst consists essentially of rhodium or consists essentially of rhodium supported on support selected from the group consisting of carbon and alumina, and under conditions to produce a product comprising at least 25 mole % methyl acetate; and a. hydrogenating said methyl acetate to produce ethanol.

* * * * *